(12) United States Patent
Ryan et al.

(10) Patent No.: US 11,944,741 B2
(45) Date of Patent: Apr. 2, 2024

(54) MEDICAL TREATMENT SYSTEMS AND RELATED METHODS THEREOF

(71) Applicant: Boston Scientific Scimed, Inc., Maple Grove, MN (US)

(72) Inventors: Shawn Ryan, Littleton, MA (US); John Thomas Favreau, Shrewsbury, MA (US); Kira Sullivan, Duxbury, MA (US); Collin Murray, Bolton, MA (US); Ashrita Raghuram, Aurora, IL (US); Alexandra Haugen, Westborough, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 18/156,673

(22) Filed: Jan. 19, 2023

(65) Prior Publication Data
US 2023/0149621 A1    May 18, 2023

Related U.S. Application Data

(63) Continuation of application No. 17/186,172, filed on Feb. 26, 2021, now Pat. No. 11,583,624.
(Continued)

(51) Int. Cl.
*A61M 1/00* (2006.01)
*A61F 13/02* (2006.01)
*A61F 13/0206* (2024.01)

(52) U.S. Cl.
CPC ........... *A61M 1/90* (2021.05); *A61F 13/0206* (2013.01); *A61F 13/0216* (2013.01)

(58) Field of Classification Search
CPC ............ A61M 1/90; A61M 1/84; A61M 1/87; A61M 1/916; A61M 27/00;
(Continued)

(56) References Cited

U.S. PATENT DOCUMENTS 2,057,206 A    10/1936   Pohl
5,451,204 A *  9/1995   Yoon ................ A61B 17/12022
                                                     600/572
(Continued)

FOREIGN PATENT DOCUMENTS

DE    102008061536 A1    6/2010
EP         2394677 A1   12/2011
(Continued)

OTHER PUBLICATIONS

International Search Report and Written Opinion for PCT/US2021/019767 dated Jun. 11, 2021 (12 pages).

*Primary Examiner* — Nicholas J. Weiss
*Assistant Examiner* — Brandon W. Levy
(74) *Attorney, Agent, or Firm* — Bookoff McAndrews, PLLC

(57) ABSTRACT

A medical system including a compressible device, and a covering over the compressible device, wherein the covering includes a delivery configuration and a deployed configuration, wherein, in the delivery configuration, the covering at least partially covers the compressible device to maintain the compressible device in a compressed state, and wherein, in the deployed configuration, the covering is releasable from the device to transition the compressible device from the compressed state to an expanded state.

20 Claims, 4 Drawing Sheets

Related U.S. Application Data

(60) Provisional application No. 62/982,206, filed on Feb. 27, 2020.

(58) Field of Classification Search
CPC ............ A61M 2210/1021; A61M 1/92; A61M 1/915; A61M 25/0071; A61M 1/80; A61M 1/77; A61M 1/85; A61F 13/0206; A61F 13/0216; A61F 13/00068; A61F 2013/0054; A61F 2250/0069; A61B 1/00; A61B 1/2736; A61B 17/0057; A61B 17/1355; A61B 17/00234; A61B 17/0218; A61B 17/12136
See application file for complete search history.

(56) References Cited

U.S. PATENT DOCUMENTS

| | | |
|---|---|---|
| 6,123,697 A | 9/2000 | Shippert |
| 10,058,413 B2 | 8/2018 | Heiss |
| 10,779,928 B2 | 9/2020 | Heiss |
| 2007/0219497 A1* | 9/2007 | Johnson ................ A61M 1/964 604/131 |
| 2013/0023840 A1* | 1/2013 | Loske .................... A61B 17/22 604/319 |
| 2015/0306287 A1 | 10/2015 | Burdick |
| 2017/0007752 A1 | 1/2017 | Freedman et al. |
| 2019/0060609 A1 | 2/2019 | Loske |
| 2020/0276056 A1 | 9/2020 | Leeds |

FOREIGN PATENT DOCUMENTS

| | | | |
|---|---|---|---|
| EP | 3134143 A1 | 3/2017 | |
| GB | 201834 A | 8/1923 | |
| WO | WO-2010063466 A1 * | 6/2010 | ....... A61F 13/00017 |
| WO | 2015164801 A1 | 10/2015 | |
| WO | 2019059893 A1 | 3/2019 | |

* cited by examiner

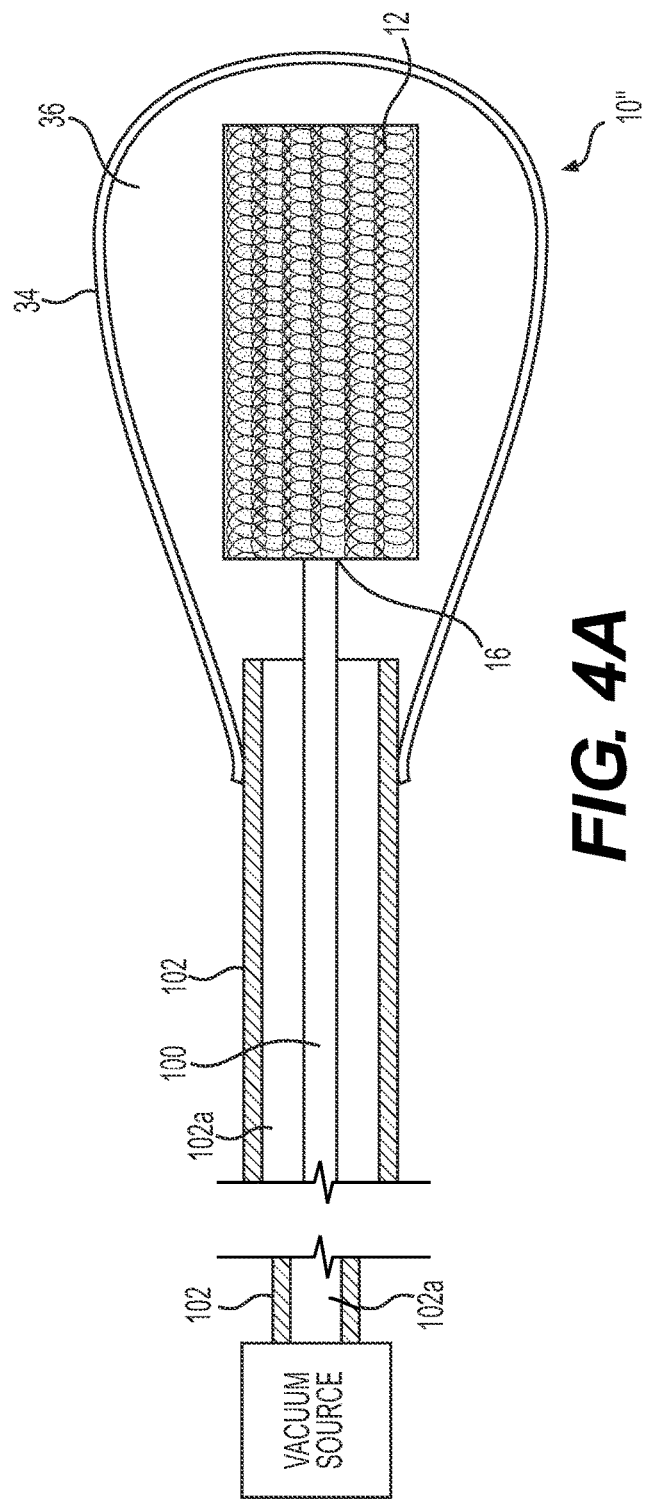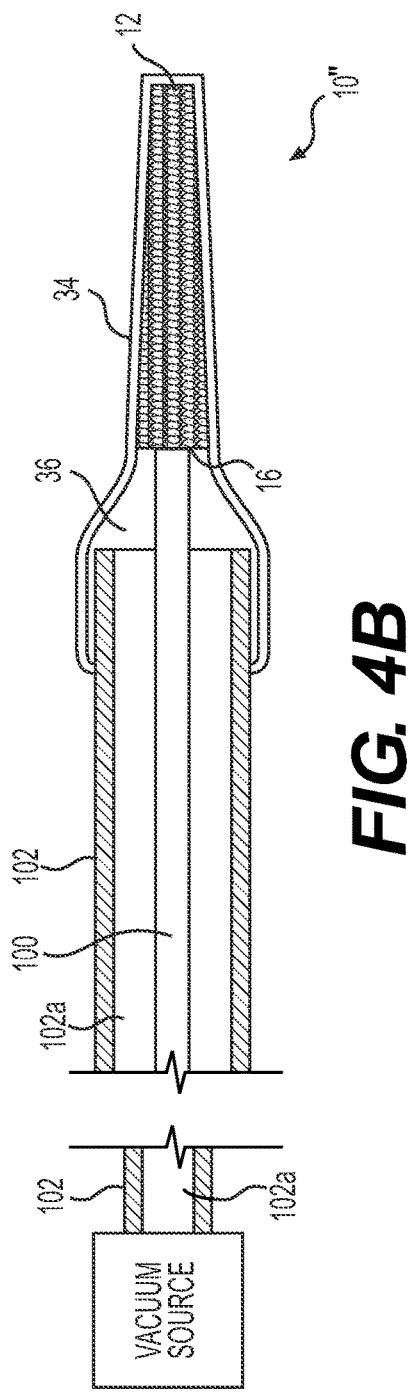

MEDICAL TREATMENT SYSTEMS AND RELATED METHODS THEREOF

CROSS-REFERENCE TO RELATED APPLICATIONS

This application is a continuation of U.S. application Ser. No. 17/186,172, filed on Feb. 26, 2021, and now pending, which claims the benefit of priority from U.S. Provisional Application No. 62/982,206, filed on Feb. 27, 2020, each of which is incorporated by reference herein in its entirety.

TECHNICAL FIELD

This disclosure relates generally to medical treatment systems, devices, and related methods thereof. Embodiments of the disclosure relate to endoluminal wound treatment systems, and medical devices for negative pressure wound therapy.

BACKGROUND

Endoscopic and open surgical procedures of the gastrointestinal (GI) tract include, for example, colonic resection, bariatric surgery, esophagectomy, gastric bypass, and sleeve gastrectomy, among others. These procedures may result in perforation, post-surgical leaks, or other wounds of the tract. Limited treatment options exist for managing such wounds, which have significant morbidity and mortality rates. Options include surgical re-operation and endoscopic placement of a stent or clips. Surgery is relatively invasive and also has high morbidity and mortality rates. Endoscopic stent placement is a less invasive option. The placed stent, however, can migrate from the intended location and/or wall off infection at the treatment site, inhibiting drainage.

SUMMARY OF THE DISCLOSURE

According to an example, a medical system may comprise a compressible device, and a covering over the compressible device, wherein the covering includes a delivery configuration and a deployed configuration, wherein, in the delivery configuration, the covering at least partially covers the compressible device to maintain the compressible device in a compressed state, and wherein, in the deployed configuration, the covering is releasable from the device to transition the compressible device from the compressed state to an expanded state.

In another example, the medical system may further comprise a suction tube, wherein the suction tube is connected to a proximal portion of the compressible device, and the suction tube is configured to apply a suction to the compressible device.

In another example, the compressible device may be porous and absorbent.

In another example, the covering may be a capsule. The capsule may be removable via exposure to a fluid.

In another example, the covering may be a netting. The medical system may further comprise a thread or a wire coupled to the netting, wherein the thread or the wire is configured to remove the netting via a force applied to the thread or the wire. The netting may be configured to be removable when the compressible device pushes against a breaking point of the netting. The netting may be configured to be tightened to further compress the compressible device.

In another example, the covering may be a membrane. The membrane may be impermeable. The membrane may be configured to compress the compressible device via a vacuum seal. The membrane may be removable via exposure to a fluid. The membrane may be configured to be removable when the compressible device pushes against a breaking point of the membrane.

In another example, the covering may completely cover the compressible device.

According to another example, a medical system may comprise a compressible device, a covering over the compressible device, a first tube connected to a proximal portion of the compressible device, and a second tube including a lumen containing the first tube, wherein a proximal end of the lumen is configured to be in communication with a suction source, wherein the covering is fixed to a distal portion of the second tube to contain and seal the compressible device within a cavity of the covering, and the covering is configured to collapse onto the compressible device via a suction supplied to the cavity, thereby compressing the compressible device. The covering may be an impermeable membrane. The compressible device may be configured to compress so that the compressible device fits within the lumen of the second tube. The covering may be configured to be removable from the second tube.

According to another example, a method of endoluminal wound treatment via a medical device, the medical device including a compressible device, a covering over the compressible device, and a tube connected to the compressible device, may comprise positioning the medical device within a cavity of a wound, removing the covering over the compressible device, and providing a suction throughout the compressible device via the tube.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIGS. 4A-4B are cross-sectional views of a medical device in expanded and compressed states, respectively, for endoluminal vacuum therapy, according to another embodiment.

DETAILED DESCRIPTION

Figure 1:
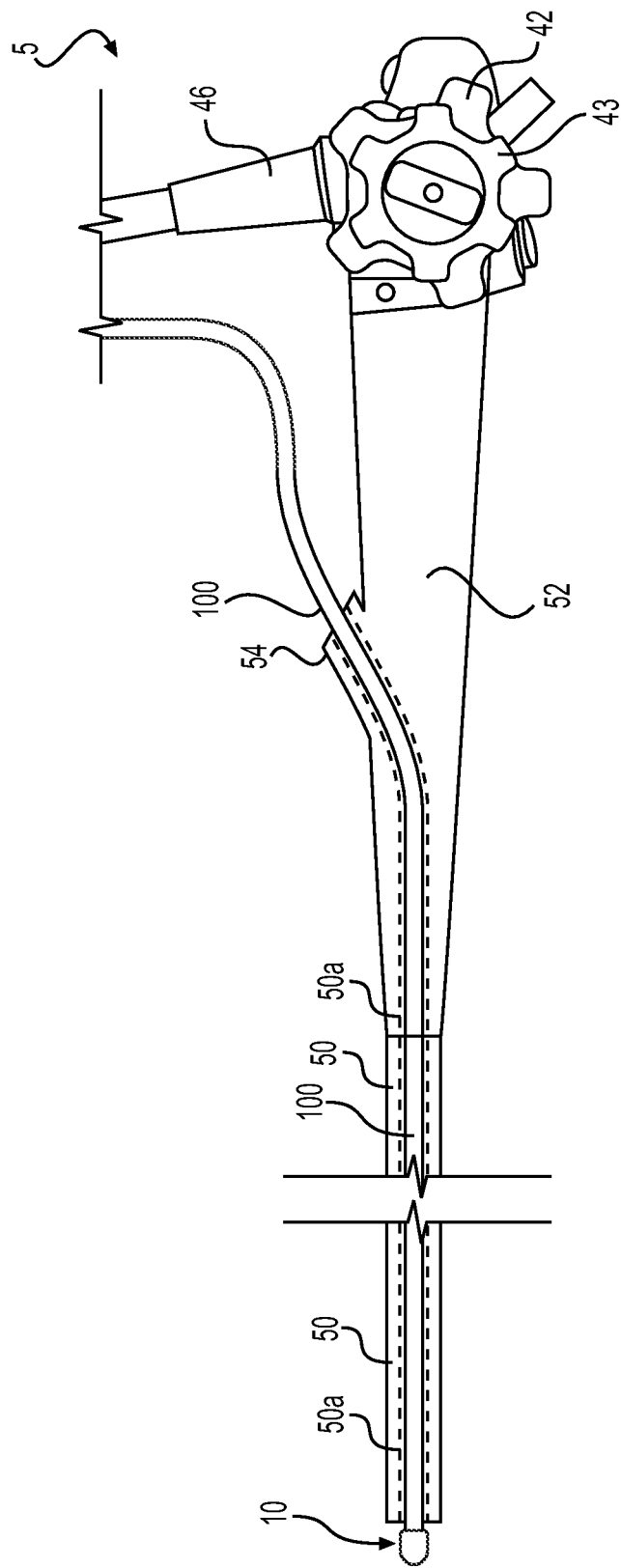
FIG. 1 is a side view of a portion of a shaft of an endoscope including a medical device for endoluminal wound treatment, according to an embodiment.

Reference will now be made in detail to aspects of the disclosure, examples of which are illustrated in the accompanying drawings. Wherever possible, the same or similar reference numbers will be used through the drawings to refer to the same or like parts. The term "distal" refers to a portion farthest away from a user when introducing a device into a subject (e.g., patient). By contrast, the term "proximal" refers to a portion closest to the user when placing the device into the subject.

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises a list of elements does not include only those elements, but may include other elements not expressly listed or inherent to such a process, method, article, or apparatus. In this disclosure, relative terms, such as, for example, "about," "substantially," "generally," and "approximately" are used to indicate a possible variation of ±10% in a stated value or characteristic.

Embodiments of this disclosure include devices, systems, and methods for endoluminal vacuum therapy (EVAC). In examples, EVAC includes endoluminal placement of a sponge or other like material into a wound site, including a perforation, a leak, an anastomosis, etc. Placement of the material may be via a catheter, scope (endoscope, bronchoscope, colonoscope, gastroscope, duodenoscope, etc.), tube, or sheath, inserted into the GI tract via a natural orifice. The orifice can be, for example, the nose, mouth, or anus, and the placement can be in any portion of the GI tract, including the esophagus, stomach, duodenum, large intestine, or small intestine. Placement also can be in other organs reachable via the GI tract. Then, negative pressure may be delivered to the wound site in the GI tract, via a vacuum source.

Furthermore, in embodiments of this disclosure, the sponge of the EVAC devices may be any suitable biocompatible material that may absorb liquids and/or permit liquid to pass therethrough via negative pressure. The material may be flexible, compressible, porous, hydrophilic, sterile, and/or disposable. The sponge material may be an open-cell foam. Suitable materials include polyurethanes, esters, ethers, composite materials, and any medical-grade material.

In the embodiments described below, the compressible sponge is in a compressed state, via varying means and mechanisms, e.g., a covering, a membrane, etc. This is so that the compressed sponge may be more easily deliverable through a working channel of a scope, and through a natural body lumen of a subject. The covering is configured to be releasable or removable in any suitable manner, e.g., sheared, broken, dissolved/degraded, so that the compressed sponge may deploy and expand once delivered to a targeted site.

Referring to FIG. 1, a medical system 5 including a scope, e.g., an endoscope, according to an embodiment is shown. Medical system 5 includes a flexible shaft 50 (e.g., a catheter) and a handle 52 connected at a proximal end of flexible shaft 50. Handle 52, or some other device for actuating or controlling medical system 5 and any tool or devices associated with medical system 5, includes first and second actuating devices 42, 43, which control articulation of flexible shaft 50, and/or an articulation joint at a distal end of flexible shaft 50, in multiple directions. Devices 42, 43, may be, for example, rotatable knobs that rotate about their axes to push/pull actuating elements (not shown). The actuating elements, such as cables or wires suitable for medical procedures (e.g., medical grade plastic or metal), extend distally from a proximal end of medical system 5 and connect to flexible shaft 50 to control movement thereof. Alternatively, or additionally, a user may operate actuating elements independently of handle 52. Distal ends of actuating elements may extend through flexible shaft 50 and terminate at an articulation joint and/or a distal tip of flexible shaft 50. For example, one or more actuating elements may be connected to an articulation joint, and actuation of actuating elements may control the articulation joint or the distal end of flexible shaft 50 to move in multiple directions.

In addition, one or more electrical cables (not shown) may extend from the proximal end of system 5 to the distal end of flexible shaft 50 and may provide electrical controls to imaging, lighting, and/or other electrical devices at the distal end of flexible shaft 50, and may carry imaging signals from the distal end of flexible shaft 50 proximally to be processed and/or displayed on a display. Handle 52 may also include ports 54, 46 for introducing and/or removing tools, fluids, or other materials from the patient. Ports 54 and/or 46 may be used to introduce tools. Ports 54 and/or 46 may also be connected to an umbilicus for introducing fluid, suction, and/or wiring for electronic components. For example, as shown in FIG. 1, port 54 receives a tube 100, which extends from the proximal end to the distal end of flexible shaft 50, via a working channel 50a of shaft 50.

As shown in FIG. 1, system 5 may be a means by which tube 100 and a medical device 10 may be delivered within the body of a subject. Tube 100 is not particularly limited. For example, tube 100 may have a single lumen (not shown) configured to be connected to a vacuum source (not shown) at its proximal end. The distal end of tube 100 is coupled to medical device 10. Thus, the lumen of tube 100 may establish communication between a vacuum source and medical device 10. This communication may be established after medical device 10 and tube 100 are delivered within the body of a subject, and removed from medical system 5. Alternatively, this communication may be established while medical device 10 and tube 100 remain within medical system 5. In other embodiments, tube 100 remains in the body of the subject, exiting the subject through a nasogastric tube. The method of placement and delivery is not limited. The medical device 10 then may administer negative pressure to a surrounding wound, thereby assisting device 10 in absorbing and suctioning any fluids from the wound. Furthermore, the application of negative pressure to a wound, via device 10, may be therapeutic and expedite the healing of the wound. The vacuum source is not particularly limited, and may be any suitable source.

Figure 2B:
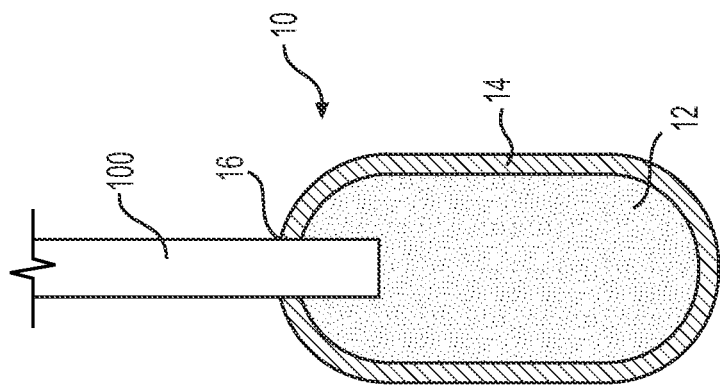
FIGS. 2A-2B are, respectively, perspective and cross-sectional views of a compressed medical device for endoluminal vacuum therapy, according to an embodiment.
Figure 2A:
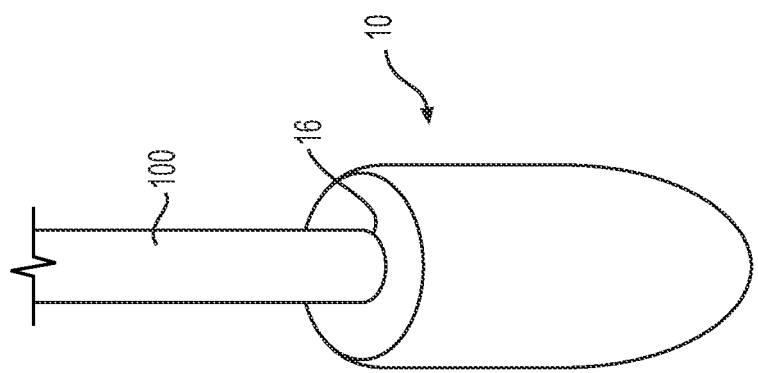

Referring to FIGS. 2A-B, an embodiment of medical device 10 of FIG. 1 is further described. Medical device 10 may be a device used for endoluminal wound treatment, e.g., an EVAC device. Thus, medical device 10 may be in a configuration in which it is deliverable to a wound, e.g., a leak, cyst, a perforation, etc., via tube 100. Device 10, once delivered to the wound, may subsequently transition into a configuration in which it is deployed, and ready for treatment.

Medical device 10 includes a compressed porous body/sponge 12, as described above, and a capsule covering 14. Sponge 12 may be compressed to an extent so that it, along with capsule 14, may fit within a working channel of any suitable scope and may be deliverable through a natural body lumen of a subject. The manner by which compressed sponge 12 is fit within capsule 14 is not particularly limited, and may be by any suitable manner. For example, sponge 12, after compression, may be inserted into an already formed capsule covering 14. In another example, sponge 12, while compressed, may be coated with a capsule coating which forms capsule covering 14.

Capsule 14 encapsulates compressed sponge 12 in its entirety, but is not limited thereto. In other exemplary embodiments, capsule 14 may cover sponge 12 partially. Capsule 14 may be of any suitable material that may withstand the expandable nature of, and outward forces generated by, compressed sponge 12. In addition, capsule 14 may be of any suitable material configured to dissolve when exposed to fluids of any sort, including fluids having a predetermined pH. Thus, for example, capsule 14 may instantly or gradually dissolve when placed into, and coming into contact with fluids within the body of a subject, via the gastrointestinal tract. Alternatively, capsule 14 may dissolve when capsule 14 is exposed to fluid, e.g., saline, from an external source, via tube 100 or another tool. Suitable materials for capsule 14 include gelatin or other collagen derivatives, hypromellose (HPMC) or other cellulose derivatives, starch, and absorbable polysaccharides. In other exemplary embodiments, capsule 14 may be formed of a suture wrapped to compress the sponge 12, or a mesh material, as described below. The thickness of the layer of capsule 14 is not particularly limited, so long as it allows for both the delivery of device 10 and the deployment of sponge 12. Suitable thicknesses of capsule 14 may be dependent on the material of capsule 14, and may include thicknesses greater than, for example, 100 microns. Thus, device 10 may include a delivery configuration, in which compressed sponge 12 is contained within capsule 14, and a deployed configuration, in which capsule 14 is removed or dissolved and sponge 12 is expanded.

Medical device 10 also includes an opening 16, through which an end of tube 100 may be inserted and thus connected to device 10. Opening 16 extends through both capsule 14 and sponge 12. Opening 16 may be on a proximal end/surface of device 10. Opening 16 may be of any suitable diameter that allows for a secure fit over tube 100. Additionally, opening 16 may be of any suitable depth that also allows for a secure fit over tube 100, while also allowing for a sufficient amount of negative pressure to be distributed throughout device 10 when deployed in a wound. The sponge 12 may be connected to the tube 100 such that the interconnected channels, open cells, or continuous passages in the sponge 12 allow for fluid and materials to be suctioned into the tube 100.

The manner and order in which medical device 10 is formed is not particularly limited. In some exemplary embodiments, opening 16 may be formed in sponge 12, prior to compression of sponge 12, and tube 100 may be inserted into opening 16. Sponge 12 may then be compressed, for example by dehydrating sponge 12 and/or applying suction to sponge 12, to close pores and channels within sponge 12. During or after compression, capsule 14 may be fitted or formed over compressed sponge 12, while accommodating for tube 100. Capsule may be placed over sponge 12 via any suitable method, including coating, e.g., spray coating, dip coating, etc., or wrapping.

Referring to FIGS. 1 and 2A-B, an example of how medical device 10 may be delivered and used is further discussed below. A user may deliver device 10, while in its delivery configuration, into the body of a subject, e.g., via a natural orifice (such as a mouth or anus). Device 10 may traverse through a tortuous natural body lumen of the subject, such as an esophagus, stomach, colon, etc. Device 10, via tube 100, may be delivered in any suitable way, for example, through working channel 50a of endoscope 5, by inserting device 10, including tube 100, into port 54 of endoscope 5. Alternatively, device 10 and tube 100 may be placed in a patient via a nasogastric tube. A user may direct/position device 10 within the wound, e.g., perforation, leak, cyst, cavity, for endoluminal wound treatment. A user may then transition device 10 to a deployed configuration by exposing capsule 14 to fluid within the body or from an external source, thereby removing capsule coating 14. Compressed sponge 12 may subsequently expand within the wound, for example, until it applies suitable pressure against the walls of the wound. A user may then remove endoscope 5 from the delivered tube 100 and device 10. Subsequently thereafter, a user may couple the proximal end of tube 100 to a vacuum source, and then turn on the vacuum source at any suitable time to supply suction or negative pressure to sponge 12, via a lumen of tube 100. Alternatively, a user may start supply of suction while device 10 is in a delivery configuration.

Figure 3:
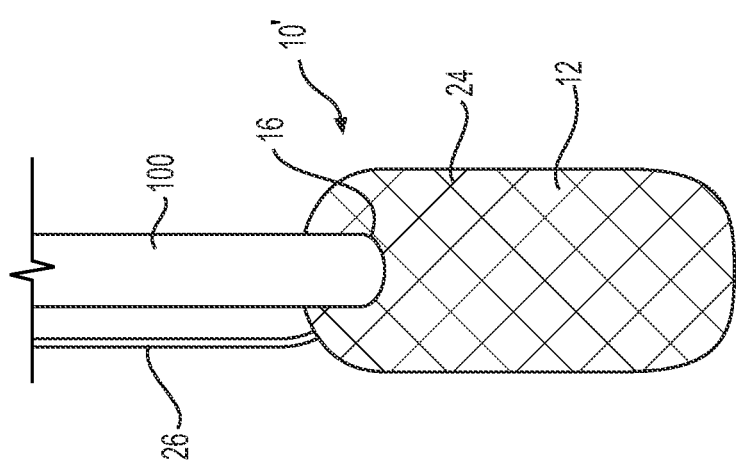
FIG. 3 is a perspective view of a compressed medical device for endoluminal vacuum therapy, according to another embodiment.

Medical device 10', as shown in FIG. 3, is similar to device 10 in many respects. Like reference numerals refer to like parts. Differences between device 10 and device 10' will be described below. Instead of a capsule coating, device 10' includes a netting 24 wrapped around sponge 12. Like capsule 14 of device 10, netting 24 may be implemented to compress sponge 12 and to contain sponge 12, via the mechanical pressure of netting 24, while holding its shape. Netting 24 may compress and contain sponge 12 so that device 10' may be deliverable through a working channel of a scope, e.g., endoscope 5. Netting 24 may be of any suitable materials and is not particularly limited. Suitable materials for netting 24 include any suitable polymer, such as nylon or polypropylene. Furthermore, the manner in which netting 24 is netted is not particularly limited as well. Netting 24 may be applied in a spiral, criss-cross, irregular, or other pattern, via any suitable method.

Device 10' further includes a control thread or wire 26 that is coupled to netting 24. Wire 26 is coupled to a proximal portion of netting 24 in FIG. 3, but is not limited thereto. Control wire 26 may be a strand(s) of netting 24, or a separate thread or wire component. Wire 26 may be configured to shear or remove netting 24 by a suitable force applied to wire 26, e.g., a pulling force. Wire 26 may extend through a lumen of tube 100 (not shown) or outside a lumen of tube 100 as shown, and a proximal end of wire 26 may be connected to a controller or mechanism (not shown) configured to exert the necessary force on wire 26 to remove netting 24. Alternatively, the proximal end of wire 26 may be free and pulled proximally by the user. Thus, wire 26 may assist in transitioning device 10' from a delivery configuration to a deployed configuration. In embodiments, the netting may be formed of a material that will degrade or dissolve upon contact with fluid.

However, device 10' is not limited to including a control wire 26. In some other exemplary embodiments, device 10' may be without wire 26, and may include other suitable mechanisms configured to remove netting 24 and deploy sponge 12. For example, netting 24 may include a breaking point, e.g., a stress riser, so that netting 24 may fracture when sponge 12 is advanced and pressed against said breaking point of netting 24. In some exemplary embodiments, such a breaking point may be found on the distal end of netting 24. Alternatively, netting 24 may be severed from sponge 12 via an endoscopic scissor or other tool.

Like device 10, the manner and order in which medical device 10' is formed is not particularly limited. In some exemplary embodiments, opening 16 may be formed in sponge 12, prior to compression of sponge 12, and tube 100 may be inserted into opening 16. Sponge 12 may then be compressed, for example by application of suction. After compression, netting 24 may be fitted over compressed sponge 12, while accommodating for tube 100. In other exemplary embodiments, netting 24 may be fitted over sponge 12 prior to compression, and netting 24 may be tightened to mechanically compress and contain sponge 12.

Device 10' may be used in a similar manner as device 10, except a user may transition device 10' to a deployed configuration by removing netting 24, via wire 26 or any other suitable manner/mechanism.

Medical device 10", as shown in FIGS. 4A-B, is also similar to device 10 in many respects. Like reference numerals refer to like parts. Differences between device 10 and device 10" will be described below. Instead of a capsule coating, device 10" includes a membrane 34. Membrane 34 is not particularly limited, and may be of any suitable impermeable material, e.g., flexible plastic, latex, etc. Membrane 34 may be flexible and/or elastic. The thickness of membrane 34 is not particularly limited as well. Membrane 34 encapsulates sponge 12 by being fixed to a distal portion of the outside of a delivery tube/catheter 102. Membrane 34 may be fixed around a complete circumference of the distal portion of catheter 102. Catheter 102 may be flexible and sized to fit within working channel 50a of scope 50. Catheter 102 includes an inner channel 102a that receives tube 100. Tube 100 moves axially within channel 102a. As shown in FIG. 4A, membrane 34 may form a cavity 36 containing sponge 12, in a non-compressed state.

Catheter 102 may be connected to a vacuum source so that channel 102a is in fluid communication with cavity 36 formed by membrane 34. To transition device 10" from a default, expanded configuration to the compressed, delivery configuration, the vacuum source may transmit suction distally, through channel 102a and down to cavity 36 of device 10". As a result of the suction and impermeable membrane 34 being fixed to catheter 102, membrane 34 collapses onto sponge 12, thereby compressing sponge 12 uniformly, as shown in FIG. 4B. Compressed sponge 12 may then be retracted into channel 102a to maintain its compressed state, by pulling tube 100 proximally. Membrane 34 may subsequently be removed or may be maintained. Device 10" may be placed into such a delivery configuration during the manufacture of the device. This may enable sponge 12 to be loaded into a delivery system with reduced tensile forces, thus potentially preventing damage. Alternatively, device 10" may be maintained in the state as illustrated in FIG. 4B. However, maintaining device 10" in the delivery configuration shown in FIG. 4B may require that suction, through working channel 50a, be continuously transmitted, if sponge 12 does not tolerate compression for an extended duration. Alternatively, membrane 34 may be of such a material that maintains its compressed configuration of FIG. 4B in the absence of suction.

The deployed configuration of device 10" is not particularly limited. For example, when compressed sponge 12 is retracted within channel 102a, as described above, sponge 12 may be extended distally out of catheter 102 to be deployed within the targeted wound. In instances in which membrane 34 is maintained, the distal end of membrane 34 may be slit (e.g. perforated or having a weakened region) so that sponge 12 may be deployed through the slit. In other examples, when device 10" is maintained in the configuration as shown in FIG. 4B, membrane 34 may be removed when device 10" is delivered to the targeted wound. The manner by which membrane 34 may be removed is not particularly limited, for example an additional tool (such as a grasper) may be used. In some exemplary embodiments, membrane 34 may be of a biodegradable material, so that membrane 34 may dissolve as it reaches the targeted wound. In other exemplary embodiments, membrane 34 may include a means by which it may break or rupture, e.g., perforations or thinned portions, so that membrane 34 may break or rupture as sponge 12 is driven forward (distally). Compressed sponge 12, once deployed, may naturally expand to its pre-compressed state until it reaches its fully expanded state and/or applies pressure against the walls of the wound area. In another embodiment, catheter 102 may be omitted from the embodiment of FIGS. 4A-4B, and membrane 34 may be fixed around a complete circumference of a distal portion of tube 100. Suction applied through tube 100 will collapse membrane 34 and compress sponge 12.

Device 10" may be used in a similar manner as device 10, except a user may transition device 10" to a deployed configuration by removing or breaking membrane 34, via the above described manners or mechanisms.

It will be apparent to those skilled in the art that various modifications and variations can be made to the disclosed device without departing from the scope of the disclosure. Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A medical system, comprising:
   a compressible device;
   a covering over the compressible device;
   a first tube connected to a proximal portion of the compressible device; and
   a second tube including a lumen containing the first tube,
      wherein a proximal end of the lumen is connected to a suction source to apply suction through the lumen exterior of the first tube,
      wherein the covering is fixed to a distal portion of the second tube to contain and seal the compressible device within a cavity of the covering, and
      wherein the covering is configured to collapse onto the compressible device via a suction supplied to the cavity, thereby compressing the compressible device.

2. The medical system of claim 1, wherein the covering is an impermeable membrane.

3. The medical system of claim 1, wherein the compressible device is configured to compress such that the compressible device fits within the lumen of the second tube.

4. The medical system of claim 1, wherein the covering is configured to be removable from the second tube.

5. The medical system of claim 1, wherein the covering is fixed around a complete circumference of the distal portion of the second tube.

6. The medical system of claim 1, wherein the compressible device is configured to be compressed uniformly.

7. The medical system of claim 1, wherein a distal end of the covering includes a weakened region.

8. The medical system of claim 7, wherein the covering is configured to be broken at the weakened region thereby forming an opening at the distal end of the covering.

9. The medical system of claim 8, wherein the compressible device is configured to be deployed through the opening at the distal end of the covering.

10. The medical system of claim 1, wherein the covering is configured to maintain a compressed configuration of the compressible device when the suction source is removed.

11. The medical system of claim 1, wherein the covering includes a biodegradable material configured to dissolve within a body of a patient.

12. A medical system, comprising:
    a compressible device;
    a covering over the compressible device;
    a first tube connected to a proximal portion of the compressible device; and a second tube including a lumen containing the first tube,
wherein a proximal end of the lumen is connected to a suction source to apply a suction through the lumen exterior of the first tube,
wherein a distal end of the covering includes a weakened region, and
wherein the covering is configured to be broken at the weakened region thereby forming an opening at the distal end of the covering.

13. The medical system of claim 12, wherein the compressible device is configured to be deployed through the opening at the distal end of the covering.

14. The medical system of claim 12, wherein the weakened region includes one of a slit or a perforation.

15. The medical system of claim 12, wherein the compressible device is configured to be transitioned from an expanded configuration to a compressed configuration when the suction is supplied to the covering via the suction source.

16. The medical system of claim 12, wherein the covering is configured to collapse onto the compressible device via the suction applied to the covering, thereby compressing the compressible device.

17. The medical system of claim 12, wherein the second tube is a catheter, wherein the suction source is configured to be coupled to the catheter, and wherein the covering is configured to be coupled to the catheter.

18. The medical system of claim 12, wherein the covering is fixed to a distal portion of the second tube to contain and seal the compressible device within a cavity of the covering.

19. A method of endoluminal wound treatment via a medical device, the medical device including a compressible device, a covering over the compressible device, a first tube connected to the compressible device, and a second tube including a lumen containing the first tube, the method comprising:
positioning the compressible device within a cavity of a wound; and
applying a suction directly from a distal opening of the second tube to a cavity of a covering exterior of and enclosing the compressible device, thereby collapsing the covering such that the compressible device is transitioned from an expanded configuration to a collapsed configuration.

20. The method of claim 19, wherein the covering incudes a weakened region, and wherein the method further comprises breaking the covering at the weakened region to form an opening, and deploying the compressible device through the opening.

* * * * *